United States Patent [19]

Stoffer et al.

[11] Patent Number: 4,778,910

[45] Date of Patent: Oct. 18, 1988

[54] METHOD OF MAKING ALKYLALKOXYSILANES

[75] Inventors: James O. Stoffer, Rolla; John F. Montle, Eureka, both of Mo.; Nanayakkara L. D. Somasivi, St. Paul, Minn.

[73] Assignee: Lopata Research & Development Corporation, St. Louis, Mo.

[21] Appl. No.: 133,131

[22] Filed: Dec. 14, 1987

[51] Int. Cl.$^4$ ............................. C07F 7/18; C07F 7/04
[52] U.S. Cl. ................................................... 556/470
[58] Field of Search ........................................ 556/470

[56] References Cited

U.S. PATENT DOCUMENTS

| 2,473,260 | 6/1949 | Rochow | 260/448.8 R |
| 3,557,179 | 1/1971 | Lenz et al. | 260/448.8 |
| 4,088,669 | 5/1978 | Malek et al. | 260/448.8 R |
| 4,323,690 | 4/1982 | Montle et al. | 556/470 |

FOREIGN PATENT DOCUMENTS

| 55-76891 | 6/1980 | Japan | 556/470 |
| 57-99593 | 6/1982 | Japan | 556/470 |

OTHER PUBLICATIONS

"Methyl Silicate from Silicon and Methanol", Eugene G. Rochow, published in Jun. 1948, J. Amer. Chem. Soc., vol. 70, pp. 2170–2171.
Correction Letter for "AE Publication", Methyl Silicate from Silicon and Methanol, Eugene G. Rochow, published in Dec. 1948, J. Amer. Chem. Soc., Additions and Corrections, p. 4279.
"Silicons: A Versatile Class of Polymers", Bruce B. Hardman & Re W. Shade, published Spring 1980, Materials Technology, pp. 26–31.

*Primary Examiner*—Paul F. Shaver
*Attorney, Agent, or Firm*—Rogers, Howell, Moore & Haferkamp

[57] ABSTRACT

A process is provided for making alkylalkoxysilane by reacting a $C_1$–$C_5$ alkyl alcohol in the presence of an effective catalytic amount of copper metal and an alkali metal carboxylate catalyst. Preferably, silicon and methanol are reacted in the presence of copper metal and potassium formate catalysts to produce methyltrimethyoxysilane.

24 Claims, No Drawings

METHOD OF MAKING ALKYLALKOXYSILANES

BACKGROUND OF THE INVENTION

1. Field of the Invention

The present invention relates to a new and useful catalytic process for making alkyltrialkoxysilanes. More particularly, the present invention relates to a new and useful process for making alkyltrialkoxysilanes by a direct reaction of methanol and silicon using a catalyst combination of copper and an alkali carboxylate.

2. Prior Art

U.S. Pat. No. 2,473,260 discloses that at elevated temperatures methanol and elemental silicon react in the presence of copper to produce tetramethoxysilane and hydrogen.

U.S. Pat. No. 4,323,690 discloses that certain tetraalkoxysilanes are produced by heating a lower alcohol, such as methanol and ethanol, and finely divided silicon in the presence of an alkali metal carboxylate catalyst. Small but barely detectable amounts of alkyltrialkoxysilanes are produced by such process and at a very slow rate. No copper catalyst is used in that process.

Methyltrichlorosilane and dimethyldichlorosilane are most important compounds for the production of a wide variety of industrial silicone polymers. Chlorosilanes are hydrolyzable to produce hydrogen chloride which is corrosive to processing equipment. In order to obviate the corrosion problems inherent in the handling of just mentioned chlorosilanes, methyltrimethoxysilane may be used to produce the silicone polymers. Unfortunately, methods used heretofore to make methyltrimethoxysilane are expensive and provide very little yield of the product.

Because of increasing demands for greater availability of methyltrimethoxysilane as an intermediate in the preparation of other organic silicon-containing products, polymers and reagents, and to eliminate the corrosion potential, efforts have been made to find alternative ways for economically producing methyltrimethoxysilane. It is possible to slightly increase the amount of produced methyltrimethoxysilane in the process described in U.S. Pat. No. 4,323,690 by adjusting the reaction conditions used during the reaction between methanol and silicon. Heretofore, these efforts have not been economically successful because extended reaction times at very high pressures are required to shift the reaction to produce only slightly more methyltrimethoxysilane.

SUMMARY OF THE INVENTION

The present invention provides a novel and useful process for making alkyltrialkoxysilanes of the formula $(RO)_3SiR$ and in particular methyltrimethoxysilane having the formula $(CH_3O)_3SiCH_3$. This is accomplished by reacting silicon and at least one lower alkyl primary alcohol ($C_1$-$C_5$), especially methanol, at elevated temperatures and preferably elevated pressures in the presence of a particular mixture of catalysts. The catalyst mixture includes copper and an alkali metal salt of a lower saturated fatty acid ($C_1$-$C_5$). The copper catalyst includes copper metal and compounds of copper, such as cuprous and cupric salts capable of being reduced or decomposed to copper metal under conditions of the reaction.

An alkali metal formate is the preferred carboxylate catalyst in the catalyst combination. The most preferred carboxylate catalysts are potassium formate and rubidium formate. A weight ratio of between about 1-1 and 100-1 of copper to alkali metal salt has been found to provide a substantial increase in the yield of alkyltrialkoxysilanes.

The silicon may be in a finely divided form or in the form of a particulate silicon/copper alloy.

The silicon and lower alcohol are brought into reactive contact in a reductive atmosphere with or without stirring in a heated reaction vessel, for example 140°-400° C., for sufficient time to produce an effective quantity of alkyltrialkoxysilane. Hydrogen gas is formed as a reaction product and is removed as an off gas. The reaction mixture is cooled and the pressure is released. Finally, the alkyltrialkoxysilane is separated from the reaction product.

Surprisingly, it has been found that the use of the combination of the two types of catalysts enables one to produce relatively large quantities of alkyltrialkoxysilanes as compared to substantially no amounts of alkyltrialkoxysilanes when the two catalysts are employed singly.

The alkyltrialkyoxysilanes are useful as precursors for use in the production of a large variety of organosilicon compounds, silicone polymers and the like.

DETAILED DESCRIPTION OF THE INVENTION

In accordance with the present invention certain lower alkyl alcohols are reacted in a reductive atmosphere with silicon in the presence of a combination of catalysts of copper and alkali metal carboxylate to produce tetraalkoxysilane, together with substantial amounts of alkyltrialkoxysilanes. Hydrogen is produced as a by-product. The lower alcohols include $C_1$-$C_5$ alkyl primary monohydric alkanols, such as methanol, ethanol, 1-propanol, etc. The most prefered alcohol is methanol.

The silicon, preferably of high purity, may be finely divided. Quite suitable is silicon powder with a mesh of 200 or higher. Alternatively, the copper catalyst component may be deposited on grains of silicon by reduction of a copper compound, such as cuprous acetate, cuprous chloride and the like, in the presence of powdered silicon.

As indicated above, the copper catalyst includes free copper and copper compounds which are reduced or decompose to free copper during the reaction. Such copper compounds include oxides of copper, hydroxides of copper, halides of copper, copper salts of aliphatic acids, carbonates of copper, cyanides of copper and mixtures thereof. The copper may take either the cupric or cuprous form. Free copper is the most preferred copper catalyst. As used herein the term copper catalyst and derivatives of such term refer to copper and copper compounds that convert to free copper under the conditions of the reaction.

The silicon and alcohol are reacted together preferably in amounts which are approximately stoichiometric. The amounts may vary plus or minus 10 percent from stoichiometrically equal amounts.

Since the reaction between the alcohol and silicon is normally carried out at temperatures above the boiling points of the alcahols, the reaction is generally carried out in a sealed vessel, such as an autoclave fitted with a condenser with a metering valve to maintain the pressure sufficiently high to keep the alcohol in the liquid phase, e.g., a pressure of from about 75 to about 1000 psi or higher, and to allow evolved hydrogen gas to escape, if necessary. The rate of hydrogen gas formation is an indication of the rate of the organosilane formation. Pressure of about 200 psi will be typically reached in the case of methanol and ethanol when the temperature reaches between 150° C. and 165° C. The temperature generally will be kept during the reaction between about 140° C. and 400° C., preferably between 200° C.-305° C. About 4 to 20 hours have been found to be sufficient reaction time for substantial completion of the reaction when carried out as a batch process. Pressure as high as 1000 psi or even higher can be employed if suitable high pressure equipment is used. Pressures of 100 to 300 psi are preferred because less expensive equipment is required.

After the reaction is completed, the reaction product can be subjected to conventional separation techniques, such as fractional distillation, to separate the desired alkyltrialkoxysilanes from the reaction mixture, as well as to separate other reaction products one from the other.

Various methods may be employed to effect the reaction between the silicon and the alcohol in the presence of the herein disclosed combination of catalysts. One method comprises intimately mixing silicon powder and copper powder, and thereafter sintering the mixture of powders at elevated temperatures, for example, 300°–1000° C. in a reducing atmosphere, for example, hydrogen. The resulting sintered product may then be ground into the form of small particles. The particles are combined with the alkali metal carboxylate catalyst and placed in a suitable reaction vessel, such as an autoclave or reaction tube. Substantially anhydrous or commercial grade alkanol is placed in the reaction vessel; and the resulting mixture is heated under elevated pressures and temperatures. The resulting tetramethyloxysilane and methyltrimethoxysilane may be recovered and separated one from the other by fractional distillation.

It is also possible to carry out the process as a continuous or steady state process in which the reactants are continuously being introduced into a reactor containing the catalyst combination of the present invention and the products are continuously being withdrawn. For example, methanol gas may be passed through a reaction tube heated at about 140° C. and 400° C. over a powdered silicon-copper catalyst and carboxylate catalyst mixture and; the effluent vapors from the reaction are condensed. Then, the methyltrimethoxysilane may be isolated from the condensate by conventional methods, such as by fractional distillation.

Residual alkali metal carboxylate catalysts and copper catalysts may be reused as catalysts, if desired.

In order to maintain a high rate of reaction between the silicon and the alkanols and in order to minimize caking of materials within the closed reaction vessel, it is preferred to provide effective agitation of the reaction mixture, for example with an adequate stirrer. It is also possible, but not essential, to include a surface active agent in the reaction mixture. The time required for the reaction and yield of product (based on silicon) may vary, depending, among other things, on the specific and relative proportions of alcohol employed. When methanol is used under preferred reaction conditions, substantial quantities of methyltrimethoxysilane may be obtained in as little as four hours reaction time.

The following examples describe various embodiments of the invention. Other embodiments within the scope of the claims herein will be apparent to one of ordinary skill in the art from consideration of the specification or practice of the invention disclosed herein. It is intended that the specification and the examples be considered exemplary only with the scope and spirit of the invention being indicated by the claims which follow the examples. Unless otherwise indicated all percentages herein are on a weight percent basis.

EXAMPLE 1

In this example activated silicon metal was prepared.

Eighteen grams of silicon powder of 325 mesh obtained from Alfa Chemicals was added to a solution of 5 grams of cuprous acetate and 40 ml of methanol in a one liter stainless steel autoclave reactor. The resulting mixture was stirred and heated to 250° C. under nitrogen pressure for approximately eight hours. The reactor was pressurized to approximately 200 psi at room temperature before heating. Methanol was distilled out of the reactor at the end of the reaction; and the reactor was cooled to room temperature. This reaction produced copper metal which was deposited as particles on the surface of the powdered silicon.

EXAMPLE 2

In this example, the combination of copper and potassium formate was employed as the catalyst combination in carrying out the process of the present invention.

19.6 grams of silicon/copper aloy as prepared in Example 1, 65 grams of methanol, and 0.025 gram of potassium formate were charged to a stirred autoclave and pres- surized with hydrogen to 100 psi before heating. The mixture was heated to 250° C. and the reactor pressure was increased to 900 psi at the end of the reaction. After a reaction time of 6.5 hours, the heating was discontinued and the pressure was lowered slowly to atmospheric pressure while the reactor and its contents cooled.

After the material had cooled sufficiently, it was drained into a flask; and the liquid produced was distilled under vacuum at 100° C., collected in an ice trap and analyzed by the gas chromatography internal standard method using anhydrous p-xylene as the internal standard. The hydrogen gas was vented during distillation. It was determined that the distillation product was composed of 4.3 grams of methyltrimethoxysilane (b.p. 102° C., f.p. 11° C.), 45.8 grams of tetramethoxysilane and 6.6 grams of unreacted methanol. Of the total organosilanes in the distillation product 8.5 percent was methyltrimethoxysilane. The residue at the bottom of the reactor was composed mostly of copper metal, unreacted silicon, and glassy solid polyorganosilicates.

EXAMPLE 3

When Example 2 was repeated but with no potassium formate being present, a reaction time of 6.5 hours was required to produce less than 0.1 gram of methyltrimethoxysilane and 1.3 gram of tetramethoxysilane with 60 grams of methonal recovered.

EXAMPLE 4

Example 2 was repeated using only the carboxylate catalyst (no copper catalyst). Under these conditions less than 0.1% methyltrimethoxysilane 90% tetramethoxysilane were produced.

EXAMPLE 5

Example 2 was repeated using neither carboxylate catalyst nor copper catalyst. It found that under these conditions no methyltrimethoxysilane or tetramethoxysilane was produced.

EXAMPLE 6

When Example 2 was repeated but with a reduced reaction time of 4 hours, it was found that 4.5 grams of methyltrimethoxysilane, 48.5 grams of tetramethoxysilane and 17.0 grams of methanol was in the distillation product. Of the total organosilanes in the distillation product 8.1 percent was methyltrimethoxysilane.

EXAMPLE 7

When Example 2 was repeated using nitrogen gas instead of hydrogen gas, no substantial differences in results were noted.

EXAMPLE 8

Example 2 was repeated except that the weight of potassium formate added to the autoclave was increased to 0.05 gram and the reaction time was reduced to 4.0 hours. Under these conditions 4.1 grams of methyltrimethoxysilane and 37.3 grams of tetramethoxysilane were produced; and 2.7 grams methanol was unreacted. Of the total organosilanes in the distillation product 10.7 percent was methyltrimethoxysilane.

EXAMPLE 9

Example 2 was repeated except that the reaction time was extended to 8.0 hours. Under these conditions 5.6 grams of methyltrimethoxysilane and 37.3 grams of tetramethoxysilane were produced and 1.5 gram of methanol was unreacted. Of the total organosilanes in the distillation product 14.5 percent was methyltrimethyoxysilane.

EXAMPLE 10

Example 2 was repeated except that 0.02 gram of sodium formate was used as the alkali carboxylate catalyst component and reaction time was 9.0 hours. Of the total organosilanes in the distillation product 0.8 percent was methyltrimethoxysilane.

EXAMPLE 11

Example 2 was repeated except that 0.04 gram of rubidium formate was used as the alkali carboxylate catalyst component and reaction time was 4.0 hours. Under these conditions 5.2 grams of methyltrimethoxysilane; 44.0 grams of tetramethoxysilane were produced; and 14.0 grams of methanol was unreacted. Of the total organosilanes in the distillation product 10.5 percent was methyltrimethoxysilane.

EXAMPLE 12

Example 9 was repeated except that the reaction time was increased to 8.0 hours. Under these conditions 4.8 grams of methyltrimethoxysilane and 46.8 grams of tetramethoxysilane were produced; and 0.6 gram of methanol was unreacted. Of the total organosilanes in the distillation product 9.3 percent was methyltrimethoxysilane.

EXAMPLE 13

Example 9 was repeated except that the reaction time was reduced to 2.25 hours. Under these conditions 3.4 grams of methyltrimethoxysilane and 34.9 grams of tetramethoxysilane were produced; and 12.6 grams of methanol was unreacted. Of the total organosilanes in the distillation product 6.7 percent was methyltrimethoxysilane.

EXAMPLE 14

Example 2 was repeated except that 1.0 gram of lithium formate was used as the alkali carboxylate catalyst component and the reaction time was 24 hours of the total organosilanes in the distillation product 1.3 percent was methyltrimethoxysilane.

What is claimed is:

1. In the process of making alkylalkoxysilanes by reacting a $C_1$–$C_5$ alkyl alcohol with silicon in the presence of an effective catalytic amount of copper catalyst, the improvement of employing an effective amount of an alkali metal carboxylate catalyst together with the copper catalyst.

2. The process of claim 1 wherein the ratio of copper to alkali metal carboxylate is in the range of about 1-1 to 100-1 on a weight basis.

3. A process of making methyltrimethoxysilane comprising reacting silicon and methanol in the presence of an effective catalytic amount of copper metal and an alkali metal formate at elevated temperatures and pressures.

4. The process of claim 3 wherein the ratio of copper to alkali metal formate in the range of about 1-1 to 100-1 on a weight basis.

5. The process of claim 4 wherein the alkali metal is potassium.

6. The process of claim 4 wherein the alkali metal is rubidium.

7. The process of claim 4 wherein the alkali metal is sodium.

8. The process of claim 4 wherein the alkali metal is lithium.

9. A process for making methyltrimethyoxysilane by heating silicon and methanol at a temperature of about 140°–400° C. at a pressure of about 75–1000 pounds per square inch in the presence of a catalytic amount of a mixture of metallic copper and an alkali metal formate.

10. The process of claim 9 wherein the ratio of copper to alkali metal formate is in the range of about 1-1 to 100-1 on a weight basis.

11. The process of claim 10 wherein the copper and silicon is employed as a sintered product wherein minute particles of copper are deposited on finely divided silicon 12. The process of claim 11 wherein the mixture of silicon and copper is heated in the presence of hydrogen.

13. The process of claim 9 wherein the alkali metal is potassium.

14. The process of claim 9 wherein the alkali metal is rubidium.

15. The process of claim 9 wherein the alkali metal is sodium.

16. The process of claim 9 wherein the alkali metal is lithium.

17. A process for making methyltrimethoxysilane comprising:
   (a) heating methanol and finely divided silicon in the presence of a catalyst system comprising essentially a catalytic effective mixture of copper metal and an alkali metal carboxylate; and
   (b) separating the thus-produced methyltrimethoxysilane from the reaction mixture.

18. The process of claim 17 carried out at a temperature of 140°–400° C. and at a pressure of 75–1000 pounds per square inch.

19. The process of claim 17 carried out at a temperature of 200°–300° C. and at a pressure of 100–900 pounds per square inch.

20. The process of claim 18 wherein the ratio of copper to alkali metal formate is in the range of about 1-1 to 100-1 on a weight basis.

21. The process of claim 20 wherein the alkali metal is potassium.

22. The process of claim 20 wherein the alkali metal is rubidium.

23. The process of claim 20 wherein the alkali metal is sodium.

24. The process of claim 20 wherein the alkali metal is lithium.

* * * * *